United States Patent [19]
Engel et al.

[11] Patent Number: 5,985,834
[45] Date of Patent: Nov. 16, 1999

[54] NOVA- AND DECAPEPTIDES IN THE PREPARATION OF A DRUG FOR THE TREATMENT OF AIDS

[75] Inventors: Jürgen Engel, Alzenau; Bernhard Kutscher, Maintal; Michael Bernd, Frankfurt am Main; Ulf Niemeyer, Offenbach, all of Germany

[73] Assignee: ASTA Medica AG, Germany

[21] Appl. No.: 08/569,111

[22] PCT Filed: Apr. 2, 1994

[86] PCT No.: PCT/EP94/01037

§ 371 Date: Dec. 18, 1995

§ 102(e) Date: Dec. 18, 1995

[87] PCT Pub. No.: WO95/00168

PCT Pub. Date: Jan. 5, 1995

[30] Foreign Application Priority Data

Jun. 18, 1993 [DE] Germany ............... 43 20 201

[51] Int. Cl.$^6$ .................................. A61K 38/00
[52] U.S. Cl. ............... 514/15; 514/800; 530/313; 530/328; 930/130
[58] Field of Search .................. 530/313, 328; 514/15, 800; 930/130

[56] References Cited

U.S. PATENT DOCUMENTS

| | | | |
|---|---|---|---|
| 5,068,222 | 11/1991 | Camble et al. | 514/15 |
| 5,073,624 | 12/1991 | Coy et al. | 530/313 |
| 5,198,533 | 3/1993 | Schally et al. | 530/313 |

FOREIGN PATENT DOCUMENTS

| | | |
|---|---|---|
| 0192492 | 8/1986 | European Pat. Off. . |
| 0299402 | 1/1989 | European Pat. Off. . |
| 0335726 | 10/1989 | European Pat. Off. . |
| 3823590 | 1/1989 | Germany . |
| 4223282 | 1/1993 | Germany . |
| 2257973 | 1/1993 | United Kingdom . |
| WO 90/03980 | 4/1990 | WIPO . |
| WO 92/09626 | 6/1992 | WIPO . |

OTHER PUBLICATIONS

Dialog, File 157: Aidsline, No. 93333809, Int.Conf. AIDS (Germany), Jun. 6–11, 1993, 9(1), p. 195 (Abstr.No.PO–A18–0362) see the whole document.

Dayhoff, *Atlas of Protein Sequence and Structure*, vol. 5, 1972, p. 96.

Primary Examiner—Cecilla J. Tsang
Assistant Examiner—C. Delacroix-Muirheid
Attorney, Agent, or Firm—Cushman Darby & Cushman IP Group of Pillsbury Madison & Sutro LLP

[57] ABSTRACT

Described are LHRH-antagonistic and bombesin-antagonistic nona- and decapeptides suitable for use in the preparation of a drug for the treatment of AIDS and ARC as well as for use in the preparation of an immunostimulation drug.

24 Claims, No Drawings

NOVA- AND DECAPEPTIDES IN THE PREPARATION OF A DRUG FOR THE TREATMENT OF AIDS

This application claims benefit of international application PCT/EP94/01037 filed Apr. 2, 1994

DESCRIPTION

Commencing in 1981, a growing incidence of hitherto rare, incurable infections was observed in homosexual men in New York and San Francisco. Severe defects in immune resistance were found in all patients. Soon afterwards, Luc Montagnier at the Institut Pasteur discovered a new virus, the human immunodeficiency virus, HIV).

Currently, only the didesoxynucleoside analog 3'-azido-3'-desoxythymidine (AZT) or Zidovudine (INN) is registered for the treatment of AIDS. It relieves the symptoms and prolongs the mean survival time of AIDS patients (EP-A 206 497). AZT therapy is associated with the development of resistant virus strains and serious bone marrow side effects. Further medicaments are currently undergoing clinical trials. Thus, for example, German published patent 39 35 580 describes the use of 1-octadecyl-2-methyl-glycero-3-phosphocholine for the preparation of medicaments for combating HIV infections. EP-A 493 378 describes the use of 2'-3'-dedeoxyguanosin or of mono or triphosphates of 2'-3'-dedeoxyguanosin for the same purpose. All these substances are still undergoing clinical trials and are not yet ready to be marketed.

Medicaments currently used as antiviral chemotherapy do not display the desired selectivity. There is consequently a great need for well tolerated, highly effective medicaments which not only delay the course of the illness, but also repress proliferation of the viruses and are, in addition, able to stabilise the weakened immune system of the patients.

It has now surprisingly been found in an AIDS screening trial on CEM-IW cells that the LHRH-analog decapeptides of formulae II–VIII display an anti-HIV and a growth stimulating effect on cell cultures.

The object of the invention is the preparation of a medicament based on peptide LHRH antagonists. The compounds show little toxicity, even in the highest dosages used.

The amino acid sequence of LHRH is:

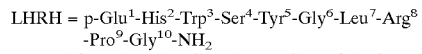
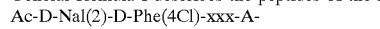
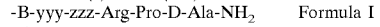

LHRH = p-Glu$^1$-His$^2$-Trp$^3$-Ser$^4$-Tyr$^5$-Gly$^6$-Leu$^7$-Arg$^8$-Pro$^9$-Gly$^{10}$-NH$_2$
General formula I describes the peptides of the invention:
Ac-D-Nal(2)-D-Phe(4Cl)-xxx-A-
-B-yyy-zzz-Arg-Pro-D-Ala-NH$_2$    Formula I
where:
xxx = D-Pal(3), D-Phe(4Cl)
yyy = D-Cit, D-Lys (R), D-Arg, D-Hci
  R may have the meanings (C$_1$–C$_4$)-acyl or
  (C$_1$–C$_{10}$)-alkyl.
zzz = L-Leu, NLe, Nva, t-Leu
A   = Ser, Ser(sugar)
  sugar may have the meanings glucose, galactose, allose,
  altrose, mannose, gulose, idose or talose
B   = Tyr, Lys(Nic), Mop
  and the pharmaceutically acceptable salts of the
  peptides such as for example hydrochloride,
  trifluoroacetate, acetate, sulfate, phosphate, mesylate
  or tosylate.

The appropriate abbreviations for amino acids, peptides and their derivatives are recommended by the IUPAC-IUB Commission for Biochemical Nomenclature. (European J. Biochem, 1984, 138, 9–37)

Abbreviations for less common amino acids:
Dpa represents 2,3-diaminopropionic acid
Nal represents 3-(2-naphthyl)-alanine,
Thi represents β-2'-thienylalanine,
Tpi represents 2,3,4,9-tetrahydro-1H-pyrido-[3,4-b]-indol-3-carboxylic acid
Nic represents Nicotinoyl
Mop represents 4-(morpholinomethyl)-phenylalanine Particularly preferred compounds according to general Formula I constitute the following amino acid sequences:

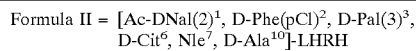
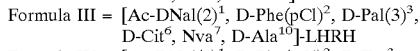
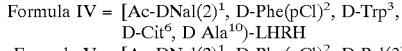
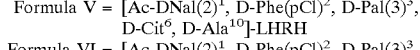
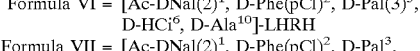
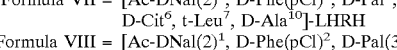
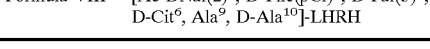

Formula II  = [Ac-DNal(2)$^1$, D-Phe(pCl)$^2$, D-Pal(3)$^3$, D-Cit$^6$, Nle$^7$, D-Ala$^{10}$]-LHRH
Formula III = [Ac-DNal(2)$^1$, D-Phe(pCl)$^2$, D-Pal(3)$^3$, D-Cit$^6$, Nva$^7$, D-Ala$^{10}$]-LHRH
Formula IV  = [Ac-DNal(2)$^1$, D-Phe(pCl)$^2$, D-Trp$^3$, D-Cit$^6$, D Ala$^{10}$)-LHRH
Formula V   = [Ac-DNal(2)$^1$, D-Phe(pCl)$^2$, D-Pal(3)$^3$, D-Cit$^6$, D-Ala$^{10}$]-LHRH
Formula VI  = [Ac-DNal(2)$^1$, D-Phe(pCl)$^2$, D-Pal(3)$^3$, D-HCi$^6$, D-Ala$^{10}$]-LHRH
Formula VII = [Ac-DNal(2)$^1$, D-Phe(pCl)$^2$, D-Pal$^3$, D-Cit$^6$, t-Leu$^7$, D-Ala$^{10}$]-LHRH
Formula VIII= [Ac-DNal(2)$^1$, D-Phe(pCl)$^2$, D-Pal(3)$^3$, D-Cit$^6$, Ala$^9$, D-Ala$^{10}$]-LHRH The oligopeptides of the invention are synthesised according to conventional processes known from the literature. A summarising description of the appropriate process is, for example, contained in M. Bodanszky, Principles of Peptide Synthesis, Springer-Verlag, Berlin, Heidelberg, New York 1984.

The principles of the solid phase synthesis of polypeptides are for example set out in the textbook by J. M. Stewart and J. D. Young, Solid Phase Peptide Synthesis, Pierce Chem. Co., Rockford, Ill., 1984 (2nd edition) and in the survey by L- Barany et al., Int.J. Peptide Protein Res. 30, 705–739 (1987).

The syntheses of the peptides according to formulae II–VIII occur according to the block diagram on methylbenzhydryl amine resin (hydrochloride commercial form) of Advanced Chem. Tech/Louisville, Kent., USA, which was converted into the free base in each case before binding of the C-terminal Boc-D-Alanin by 10% triethylamine in dichloromethane (V/V).

All the following Na-Boc-protected amino acids were coupled in threefold molar excess in the presence of diisopropyl carbodiimide (DIC) and 1-hydroxybenzotriazol (HOBt) in CH$_2$Cl$_2$/DMF within 90 minutes, in dichloromethane/dimethylformamide mixtures of the composition 80/20 (V/V) and the Boc protecting group by reaction of 50% trifluoroacetic acid (TFA) in dichloromethane for half an hour. Remains of free amino functions are blocked by acetylation in fivefold excess of acetylimidazole in dichloromethane. The sequence of the reaction steps in the resin-supported peptide synthesis is shown in the block diagram. To split the resin-bound peptides, the end product of the solid phase synthesis was in each case dried in a vacuum and treated in 500fold excess on HF/anisol 10:1 (V/V) for 45 to 60 minutes at 0° C.

After distillation of HF and anisol in a vacuum, all raw peptide amides accumulated as white solids by stirring out with anhydrous ethyl ether, the separation of also accumulating polymer carriers occurred by washing out with 50% (V/V) aqueous acetic acid. Cautious concentration of the acetate solutions in a vacuum yielded the corresponding peptides as highly viscous oils which gradually changed into white solids after the addition of absolute ether in the cold.

The raw peptides were isolated, washed on a frit with absolute ether and dried in a vacuum.

Preparative cleaning was carried out using high pressure liquid chromatography (HPLC) under the conditions cited:

Parameters for Preparative HPLC

| Apparatus: | Shimadzu LC-8A pump |
| --- | --- |
| | Shimadzu SPD-6A detector |
| | Shimadzu C-R4A integrator |
| | Shimadzu SCL-6A controller |
| Reagents: | Acetonitrile Lichrosolv Merck Art. 30 |
| | Trifluoroacetic acid Fluka No. 91700 |
| | Purest water (Seralpur installation) |
| Mobile phase A: | 970 ml water (VE water purest) |
| | +30 ml acetonitrile |
| | +1 ml trifluoroacetic acid |
| Mobile phase B: | 300 ml water (VE water, purest) |
| | +700 ml acetonitrile |
| | +1 ml trifluoroacetic acid |
| Flow rate: | 40 ml/min |
| Pressure: | 14 bar |

Average time of flow of a preparative passage: approx. 30 to 40 min.

The correct identity of all peptides synthesized was demonstrated after HPLC purification by means of amino acid analysis, mass spectrometry and $^1$H-NMR-spectroscopy.

Block diagram for the solid phase synthesis of the LH-RH peptides: the repeated working steps of the solid phase synthesis are summarised in the following diagram; steps 1 to 17 describe the requisite sequence of operating steps for attaching one amino acid in each case:

| Step | Reagents and Operations | Time [min] |
| --- | --- | --- |
| 1 | Boc-amino acid, DIC, HOBt 1:1:1 | 90 |
| 2 | Colour test for total reaction, if positive: repeat 1 and 2 | |
| 3 | MeOH, washing | 1 |
| 4 | DIPEA, 10% in $CH_2Cl_2$; neutralisation | 2 |
| 5 | MeOH; washing | 1 |
| 6 | $CH_2Cl_2$; washing, 3-times | 2 |
| 7 | $(CH_3CO)_2O$, imidazole, 1:1, acetylation | 30 |
| 8 | MeOH; washing, twice | 1 |
| 9 | $CH_2Cl_2$; washing, 3-times | 2 |
| 10 | TFA, 50% in $CH_2Cl_2$, splitting Boc | 1 |
| 11 | TFA, 50% in $CH_2Cl_2$, splitting Boc | 30 |
| 12 | Isopropanol; washing and decolorisation | 2 |
| 13 | DIPEA, 10% in $CH_2Cl_2$; neutralisation | 3 |
| 14 | MeOH; washing | 1 |
| 15 | DIPEA, 10% in $CH_2Cl_2$; neutralisation | 3 |
| 16 | MeOH; washing | 1 |
| 17 | $CH_2Cl_2$; washing, twice | 2 |

Synthesis Product According to the Above Block Diagram

D-Nal(2)-D-Phe(4Cl)-Xxx-A-B-Yyy-Zzz-Arg-Pro-D-Ala-$NH_2$
(according to Formula I)

The completeness of the synthesis was checked using the chloranil test after Th. Christensen; Acta Chem. Scand, B 33, 763 (1979) and using Kaiser's ninhydrin test after Stewart, Young.

The invention relates to a process for the preparation of a medicament for the treatment of viral infections, preferably for the treatment of AIDS. Novel peptides and their syntheses are also described which may be used for antiviral treatment. The peptides are of low toxicity, even at the highest dosage used. Compared to the reference compound azidothymidine tested at the same time, the EC50 values of the peptides tested were between $5.9 \times 10^{-7}$ mol/liter and $2.0 \times 10^{-5}$ mol/liter in the NCI experiment.

The reference compound AZT (azidothymidine) tested at the same time had, for example, an EC50 value of $3.10 \times 10^{-9}$ mol/l. All compounds were dosed in the range of $10^{-4}$ to $10^{-8}$ mol/l. The conventionally stated IC50 value (inhibitory concentration in which 50% of cells die in the non-infected culture) is therefore higher than the highest dosage.

The infected culture treated has an EC50 value of $4.5 \times 10^{-5}$ mol/l. Since the values for the treated, non-infected culture do not fall to an IC50 value, only the value for the highest dosage can be given for the IC50 value, that is IC50=>$3.3 \times 10^{-5}$ mol/l. The therapeutic index (TI 50=IC50/EC50) is then greater than 7.30.

Description of the Screening Method for Anti-HIV Activity

The process is suitable for locating active substances which are effective in all phases of the virus proliferation cycle. The test principle is based on the destruction of the T4 lymphocytes by the HIV virus.

Small amounts of HIV virus are added to the cell cultures. At least two complete viral reproduction cycles are needed to destroy the T4 lymphocytes and to be able to evaluate the results.

Active substances that react with virions (virus-like particles), cells or with products of the viral genes in order to interact with viral activities and thus block proliferation of the viruses will protect the cells from destruction and lysis.

The test system is automated to permit examination of a large number of cells infected with viruses. Compounds which degenerate, denaturise or that are rapidly metabolised cannot, however, be reliably discovered using the test procedure.

AZT (azidothymidine) and DDC serve as positive controls for the test.

Test Procedure

1. T4 lymphocytes (CEM cell line) are mixed with virus in the ratio of virus:cell of ca. 1:0.05 in microtiter plates.
2. Unless otherwise stated, the substance to be tested is dissolved in dimethylsulfoxide (DMSO) and diluted in a ratio of 1:200 (parts by weight). Other dilutions are prepared in semilogarithmic steps with DMSO and then added to infected and non-infected cell cultures.
3. The cultures are incubated for 6–7 days at 37° C. in a 5% $CO_2$ atmosphere.
4. The tetrazolium salt XTT is added to the cell cultures and the cell cultures are further incubated to run the formazan colour reaction by coupling with phenazine methosulfonate (PMS) through surviving cells.
5. The individual cell cultures are analysed spectrophotometrically and examined microscopically to detect surviving cells in order to confirm the protective effect.
6. Treated, virus-infected cells are compared with treated, non-infected cells. Other comparisons (untreated, infected cells and untreated, uninfected cells, active substance-containing, cell-free depressions) are carried out on the same plate.
7. The activity of the tested compound is determined.

The remaining experimental details may be taken from Weislow, J.Nat. Canc. Inst. 81 (8), page 577 (1989).

The peptides according to the invention are thus suitable for the preparation of medicaments for combating AIDS and for combating diseases that are associated with infection with the immune deficiency virus (AIDS-related complex, ARC).

Dosage Information

The dosage of the medicament of the invention is between 0.01 mg and 10 mg in the case of daily administration.

EXAMPLE 1

Peptide According to Formula II

Mass spectrum: [M+H$^+$]=1431

$^1$H-NMR-spectrum (DMSO-d$_6$, 250 MHz) δ in ppm: 8.65–7.1; many multiplets, aromatic and NH signals; 7.0 and 6.6, 2.1, 4H, aromatic H Tyr; 5.95 m, NHCONH$_2$ Cit; 4.8–4.1, several multiplets, C$_d$H; 3.75 and 3.5, 2 multiplets; aliphatic H;3.2–2.65, several multiplets, CβH aliphatic and aromatic amino acids; 2.1–1.3, several multiplets, residual aliphatic H; 1.780, d,3H, CH$_3$CO$^-$; 1.20, d,3H, CβHAl1a; 0.80, m, Nle.

EXAMPLE 2

Peptide According to Formula III $^1$H-NMR-spectrum (DMSO-d$_6$, 250 MHz) δ in ppm: 8.65–7.1; many multiplets, aromatic and NH signals; 7.0 and 6.6 2d, 4H, aromatic H Tyr; 5.9 m, NHCONH$_2$, Cit; 4.8–4.1, several multiplets, C$_2$H; 3.75 and 3.5, 2 multiplets; aliphatic H; 3.2–2.65, several multiplets, CβH aliphatic and aromatic amino acids; 2.1–1.25, several multiplets, residual aliphatic H; 1,70,5, 3H, CH$_3$CO$^-$; 1.20, d,3 H, CBHA,Ala; 0.85,m, 3H, Nva.

Mass spectrum: [M+H$^+$]=1417

EXAMPLE 3

Peptide According to Formula IV

Mass spectrum: [M+H+]=1469

$^1$H-NMR-spectrum (DMSO-d$_6$, 250 MHz) δ in ppm: 8.2–6.5, many multiplets, aromatic and NH signals; 5.8 and 5.4, 2 m, 3 H, NH—CO—NH$_2$ citrollia, 4.5, 4.3, 4.2 and 4.0, multiplets C$_d$H, 3.8–2.6, several multiplets; aliphatic and aromatic CβH; 2.0–1.9, several multiplets, residual aliphatic protons; 1,6,5,3 H, CH$_3$CO$^-$; 1.1, d,2H, CβH Ala; 0.7, d,6 H CδH leu

EXAMPLE 4

Peptide According to Formula V, INN: Cetrorelix

Mass spectrum: [M+H$^+$]=1431

$^1$H-NMR-spectrum (DMSO-d$_6$, 250 MHz) in ppm: 8.7–7.2, many multiplets, aromatic and NH signals; 7.05 and 6.65, 2d, 4H, aromatic H Tyr; 5.85, m NHCONH$_2$, Cit; 4.8–4.1, several multiplets; CαH; 3.8 and 3.55, 2 m aliphatic H; 3.3–2.7 CβH aliphatic and aromatic amino acids; 2.1–1.3, several multiplets, residual aliphatic signals; 1,7,5,3 H, CH$_3$CO$^-$; 1.2, d, 3 H, CβH Ala; 0.85 2d, 6H, CδH leu

EXAMPLE 5

Peptide According to Formula VI

Mass spectrum: [M+H$^+$]=1444

$^1$H-NMR-spectrum (DMSO-d$_6$, 250 MHz) δ in ppm: 8.6–7.1, many multiplets, aromatic and NH signals; 7.0 and 6.6, 2 d, 4 H, aromatic H Tyr; 4.8–4.0, several multiplets; C H; 3.7 and 3.5, 2 m 4 H; 3.2–2.7, several multiplets, CβH aromatic and aliphatic amino acids; 2.0–1.0, several multiplets, residual aliphatic signals; 1,7, 5, 3H, CH$_3$CO; 1.2,d, 3H, CβH Ala; 0.8, dd, 6H, CδH leu

EXAMPLE 6

Peptide According to Formula VII

Mass spectrum: [M+H$^+$]=1431

$^1$H-NMR-spectrum (DMSO-d$_6$, 250 MHz) in ppm: 8.6–7.1, many multiplets, aromatic and NH signals; 7.0 and 6.6, 2d, 4H, aromatic H Tyr; 5.9 m NHCONH$_2$, Cit; 4.8–4.0, several multiplets; CαH; 3.85 and 3.5, 2 multiplets, aliphatic H; 3.1–2.7 several multiplets CβH aliphatic and aromatic amino acids; 2.1–1.3, several multiplets, residual aliphatic H; 1,7,5,3 H, CH$_3$CO$^-$; 1.20, d, 3H, CβH Ala; 0.85, 5, 9H, t-butyl, Tle

EXAMPLE 7

Peptide According to Formula VIII

Mass spectrum: [M+H$^+$]=1405

$^1$H-NMR-spectrum (DMSO-d$_6$, 500 MHz) δ in ppm: 9.1–7.3, many multiplets, aromat. and NH signals; 7.21, dd,4H, aromatic H p-cl-Phe; 7.0 and 6.6, 2d, 4 H, aromatic H Tyr; 5.9 and 5,4,2m, 3H, NHCONH$_2$ Cit; 4.7–4.1, several multiplets, C H; 3.55–2.8, several multiplets, CβH aliphatic and aromatic amino acids; 1,70,5, 3H, CH$_3$CO$^-$; 1.55 and 1,45,2 m aliphatic signals Arg and Leu; 0.80, dd, 6H, CδH Leu

What is claimed is:

1. A method of combating a virus that causes a disease selected from the group consisting of AIDS and AIDS related complex (ARC) by administering a pharmaceutically effective amount of at least one peptide with an amino acid sequence according to the general Formula I Ac-D-Nal(2)-D-Phe(4-Cl)-xxx-A-B-yyy-zzz-Arg-C-D-Ala-NH$_2$ wherein xxx = D-Pal(3), [D-phe(4-Cl),] or D-Trp
yyy = D-Cit, D-Lys(R), [D-Arg] or D-Hci
    R is selected from the group consisting of C$_1$–C$_4$)-acyl and (C$_1$–C$_{10}$)-alkyl,
zzz = L-Leu, Nle, Nva, or t-Leu
A = Ser, Ser(sugar)
    wherein sugar is selected from the group consisting of glucose, galactose, allose, altrose, manose, gulose, idose and talose.
B = Tyr, Lys(Nic), or Mop
C = Pro, or Ala or a pharmaceutically acceptable salt thereof optionally inlcuding hydrochloride, trifluoroacetate, acetate, sulfate, phosphate, mesylate or tosylate.

2. The method of claim 1, wherein said pharmaceutically effective amount of said at least one peptide is effective to protect T-lymphocytes infected with said virus.

3. The method of claim 1, wherein said pharmaceutically effective amount of said at least one peptide is effective to combat said virus by inhibiting proliferation of said virus.

4. A method of combating a virus that causes a disease selected from the group consisting of AIDS and ARC by administering a pharmaceutically effective amount of at least one peptide with an amino acid sequence according to Formula II

[AC-D-Nal(2)[1], D-Phe(4-Cl)[2], D-Pal(3)[3], D-Cit[6], Nle[7], Pro[9], D-Ala[10]]-LHRH or a pharmaceutically acceptable salt thereof.

5. Method of claim 4, wherein said pharmaceutically effective amount of said at least one peptide is effective to protect T-lymphocytes infected with said virus.

6. The method of claim 4, wherein said pharmaceutically effective amount of said at least one peptide is effective to combat said virus by inhibiting proliferation of said virus.

7. A method of combating a virus that causes a disease selected from the group consisting of AIDS and ARC by administering a pharmaceutically effective amount of at least one peptide with an amino acid sequence according to Formula III

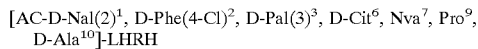

[AC-D-Nal(2)$^1$, D-Phe(4-Cl)$^2$, D-Pal(3)$^3$, D-Cit$^6$, Nva$^7$, Pro$^9$, D-Ala$^{10}$]-LHRH or a pharmaceutically acceptable salt thereof.

8. The method of claim 7, wherein said pharmaceutically effective amount of said at least one peptide is effective to protect T-lymphocytes infected with said virus.

9. The method of claim 7, wherein said pharmaceutically effective amount of said at least one peptide is effective to combat said virus by inhibiting proliferation of said virus.

10. A method of combating a virus that causes a disease selected from the group consisting of AIDS and ARC by administering a pharmaceutically effective amount of at least one peptide with an amino acid sequence according to Formula IV

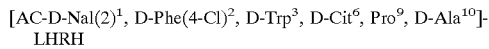

[AC-D-Nal(2)$^1$, D-Phe(4-Cl)$^2$, D-Trp$^3$, D-Cit$^6$, Pro$^9$, D-Ala$^{10}$]-LHRH or a pharmaceutically acceptable salt thereof.

11. The method of claim 10, wherein said pharmaceutically effective amount of said at least one peptide is effective to protect T-lymphocytes infected with said virus.

12. The method of claim 10, wherein said pharmaceutically effective amount of said at least one peptide is effective to combat said virus by inhibiting proliferation of said virus.

13. A method of combating a virus that causes a disease selected from the group consisting of AIDS and ARC by administering a pharmaceutically effective amount of at least one peptide with an amino acid sequence according to Formula V

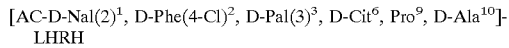

[AC-D-Nal(2)$^1$, D-Phe(4-Cl)$^2$, D-Pal(3)$^3$, D-Cit$^6$, Pro$^9$, D-Ala$^{10}$]-LHRH or a pharmaceutically acceptable salt thereof.

14. The method of claim 13, wherein said pharmaceutically effective amount of said at least one peptide is effective to protect T-lymphocytes infected with said virus.

15. The method of claim 14, wherein said pharmaceutically effective amount of said at least one peptide is effective to combat said virus by inhibiting proliferation of said virus.

16. A method of combating a virus that causes a disease selected from the group consisting of AIDS and ARC by administering a pharmaceutically effective amount of at least one peptide with an amino acid sequence according to Formula VI

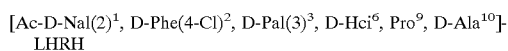

[Ac-D-Nal(2)$^1$, D-Phe(4-Cl)$^2$, D-Pal(3)$^3$, D-Hci$^6$, Pro$^9$, D-Ala$^{10}$]-LHRH or a pharmaceutically acceptable salt thereof.

17. The method of claim 16, wherein said pharmaceutically effective amount of said at least one peptide is effective to protect T-lymphocytes infected with said virus.

18. The method of claim 16, wherein said pharmaceutically effective amount of said at least one peptide is effective to combat said virus by inhibiting proliferation of said virus.

19. A method of combating a virus that causes a disease selected from the group consisting of AIDS and ARC by administering a pharmaceutically effective amount of at least one peptide with an amino acid sequence according to Formula VII

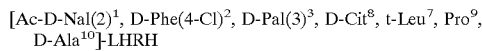

[Ac-D-Nal(2)$^1$, D-Phe(4-Cl)$^2$, D-Pal(3)$^3$, D-Cit$^8$, t-Leu$^7$, Pro$^9$, D-Ala$^{10}$]-LHRH or a pharmaceutically acceptable salt thereof.

20. The method of claim 19, wherein said pharmaceutically effective amount of said at least one peptide is effective to protect T-lymphocytes infected with said virus.

21. The method of claim 19, wherein said pharmaceutically effective amount of said at least one peptide is effective to combat said virus by inhibiting proliferation of said virus.

22. A method of combating a virus that causes a disease selected from the group consisting of AIDS and ARC by administering a pharmaceutically effective amount of at least one peptide with an amino acid sequence according to Formula VII

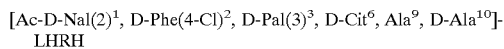

[Ac-D-Nal(2)$^1$, D-Phe(4-Cl)$^2$, D-Pal(3)$^3$, D-Cit$^6$, Ala$^9$, D-Ala$^{10}$]-LHRH or a pharmaceutically acceptable salt thereof.

23. The method of claim 22, wherein said pharmaceutically effective amount of said at least one peptide is effective to protect T-lymphocytes infected with said virus.

24. The method of claim 22, wherein said pharmaceutically effective amount of said at least one peptide is effective to combat said virus by inhibiting proliferation of said virus.

* * * * *